US010132732B2

(12) United States Patent
Xuan et al.

(10) Patent No.: US 10,132,732 B2
(45) Date of Patent: Nov. 20, 2018

(54) METHOD OF HIGH-TEMPERATURE NICKEL-BASED BOLTS BASED ON DAMAGE TOLERANCE THEORY

(71) Applicants: East China University of Science and Technology, Shanghai (CN); Shanghai Turbine Company LTD, Shanghai (CN)

(72) Inventors: Fuzhen Xuan, Shanghai (CN); Jianping Tan, Shanghai (CN); Jianguo Gong, Shanghai (CN); Xia Liu, Shanghai (CN)

(73) Assignees: East China University of Science and Technology, Shanghai (CN); Shanghai Turbine Company LTD, Shanghai (CN)

( * ) Notice: Subject to any disclaimer, the term of this patent is extended or adjusted under 35 U.S.C. 154(b) by 0 days.

(21) Appl. No.: 15/528,241

(22) PCT Filed: Jun. 1, 2016

(86) PCT No.: PCT/CN2016/084248
§ 371 (c)(1),
(2) Date: May 19, 2017

(87) PCT Pub. No.: WO2016/173567
PCT Pub. Date: Nov. 3, 2016

(65) Prior Publication Data
US 2017/0315036 A1    Nov. 2, 2017

(30) Foreign Application Priority Data
May 25, 2016  (CN) .......................... 2016 1 0353421

(51) Int. Cl.
*G01N 3/18*      (2006.01)
*G01N 33/20*    (2006.01)
(Continued)

(52) U.S. Cl.
CPC ................. *G01N 3/18* (2013.01); *B21H 1/00* (2013.01); *F16B 1/00* (2013.01); *G01M 99/00* (2013.01); *G01N 33/20* (2013.01)

(58) Field of Classification Search
CPC ........................................................ G01N 3/18
See application file for complete search history.

(56) References Cited

FOREIGN PATENT DOCUMENTS

| CN | 202720153 | 2/2013 |
|---|---|---|
| CN | 104711407 | 6/2015 |
| CN | 105039885 | 11/2015 |

OTHER PUBLICATIONS

Written Opinion in corresponding PCT Application Serial No. PCT/CN2016/084248, dated Mar. 2, 2017 (English translation attached).

(Continued)

*Primary Examiner* — Manuel A Rivera Vargas
(74) *Attorney, Agent, or Firm* — Hovey Williams LLP

(57) ABSTRACT

The invention relates to a design method of high-temperature nickel-based bolts based on damage tolerance theory, comprising the following steps: $S_1$: acquiring operating parameters for the design; $S_2$: selecting a material for bolts; $S_3$: acquiring mechanical properties of the materials; $S_4$: determining a pretension stress $\sigma_p$ of a single bolt; $S_5$: determining the service stress $\sigma_s$ under the steady state; $S_6$: determining the number n, the effective cross-section area A and the distribution of bolts; $S_7$: determining a maximum allowable crack dimension; $S_8$: calculating the maximum allowable service stress $\sigma_{th}$ using the crack propagation threshold $K_{th}$ at the design temperature; $S_9$: comparing the service stress $\sigma_s$ and the maximum allowable service stress $\sigma_{th}$, if $\sigma_s$ is smaller than $\sigma_{th}$, then the bolts are safe in the design life; otherwise, return to step $S_4$ and reduce the pretension stress $\sigma_p$.

9 Claims, 4 Drawing Sheets

(51) Int. Cl.
    *B21H 1/00*     (2006.01)
    *F16B 1/00*     (2006.01)
    *G01M 99/00*     (2011.01)

(56) References Cited

OTHER PUBLICATIONS

International Search Report in Corresponding PCT Application Serial No. PCT/CN2016/084248, dated Mar. 2, 2017, 8 pages (English translation attached).

METHOD OF HIGH-TEMPERATURE NICKEL-BASED BOLTS BASED ON DAMAGE TOLERANCE THEORY

RELATED APPLICATIONS

This application is the National Stage of International Patent Application No. PCT/CN2016/084248, filed Jun. 1, 2016, which claims priority to Chinese Patent Application No. 201610353421.1, filed May 25, 2016, each of which is hereby incorporated by reference in its entirety.

TECHNICAL FIELD

The invention pertains to the field of nickel-based bolts, and relates to a design method for resistance to fracture of nickel-based bolts at high temperature, more particularly to a design method of bolts using nickel-based alloys with high strength and low resistance to fracture at high temperature, such as nickel-based high-temperature bolts, studs, nuts, etc.

BACKGROUND OF THE INVENTION

In compliance with the principles of energy saving, consumption reduction, high efficiency and environmental protection, higher temperature, higher pressure and longer service life represent a developmental trend of devices in the fields of electric power, refining and chemicals, metallurgy, aviation, etc. For example, a single ultra-supercritical generator unit in a power plant has a power of 1000 MW or more, operating parameters of 600-650° C./32-35 MPa, and a design life of 30 years. An advanced turbine of an aero-engine has a front inlet temperature of up to 1980-2080° C., a thrust weight ratio of 15-20 or more, and a maximum service life of more than 40000 hours. The 700° C. thermal power and 4th generation nuclear power technologies under development with great efforts nowadays are also based on high temperature and pressure parameters and a long design life. With increasing promotion of the operating parameters of the devices, heat resisting materials such as ferrite steels, martensite steels and austenite steels cannot continue to meet the operating requirements of the various components. The effectuation of these process devices entails substantial use of nickel-based alloys with higher strength and better creep characteristics at high temperature.

Nickel-based high-temperature bolt, using nickel-based alloys as raw materials, is the generic term for all types of mechanical parts used to fasten and connect two or more elements as a whole at high-temperature environment. They mainly include bolts, studs, nuts, etc., widely used in the fields of energy, refining and chemicals, metallurgy, aviation, etc.

The current design methods for nickel-based high-temperature bolts are based on strength theories, and have the following general procedure: acquiring operating parameters; selecting a material; determining the pretension force; determining an arrangement and dimension of the bolts; analyzing the stress applied on the bolts; and checking the strength under various working conditions (considering the influence of relaxation).

However, fracture incidents of nickel-based high-temperature bolts occur from time to time. For example, some steam turbine bolts made of GH4145 alloy fractured in Jingyuan Second Power Co., Ltd. (2011); and a batch of bolts composed of Inconel 783 alloy cracked in several ultra-supercritical power generation units (2012); etc. Such incidents caused shutdown or production halt, leading to enormous economic loss. The main reason is that fracture toughness is specifically related to time and significantly reduces after a long time service of the nickel-based alloys at high temperature, although the nickel-based alloys has better high-temperature strength and anti-relaxation property. Hence, the critical point in design is to ensure that a nickel-based high-temperature bolt will not fracture in its service life. For this kind of materials with such properties, although, the conventional design methods for bolts based on strength theories appear to provide perfect safety factor, a decisive factor of the materials' fracture property is not taken into consideration in the design process, so the safe operation of a device cannot be guaranteed.

Therefore, the conventional design methods for bolts are not suitable for nickel-based bolts with superior strength and inferior resistance to fracture at high temperature. Thus, in this field, it is urgent to develop a new design method for resistance to fracture of nickel-based bolts at high temperature.

BRIEF DESCRIPTION OF THE INVENTION

In view of the features of high strength and low resistance to fracture of nickel-based alloys at high temperature, a new design method is proposed for resistance to fracture of a nickel-based bolt at high-temperature environment, and a new strength design process is provided for bolts. Thus, the existing problem is solved in conventional method.

The invention provides a design method of high-temperature nickel-based bolts based on damage tolerance theory, comprising the following steps:

$S_1$: acquiring operating parameters for the design, wherein the parameters include: the design temperature T; the environmental medium; the prospective operating life; the designation, structure and size of the material to be fastened; and the force P needed to fulfill the fastening function;

$S_2$: selecting a material for bolts according to the design temperature T and the environmental medium in step $S_1$;

$S_3$: acquiring mechanical properties of the materials, including: linear expansion coefficients $\alpha_b$ and $\alpha_v$ of the material for bolts and the material to be fastened, respectively; the elastic modulus E, tensile property, stress relaxation property, and crack propagation threshold $K_{th}$ of the bolt material at design temperature;

$S_4$: determining a pretension stress $\sigma_p$ of a single bolt according to the selected material in step $S_2$, the pretension stress can be given as $\sigma_p=0.50\ \sigma_y$, where $\sigma_y$ represents the yield strength of the bolt material;

$S_5$: determining the residual stress $\sigma_r$ after stress relaxation in the design life at the design temperature T in step $S_1$, wherein $\sigma_r$ is obtained by referring to a database of material properties, or by extrapolating or interpolating a relaxation curve obtained by a high-temperature relaxation test and plotted by using Origin software, Excel software or by hand; calculating a thermal stress $\sigma_t$ under the steady state according to $\sigma_t=E(\alpha_v-\alpha_b)T$; and determining a service stress $\sigma_s$ under the steady state, wherein $\sigma_s$ is the smaller one between $\sigma_r$ and the larger one of $\sigma_p+\sigma_t$ and $\sigma_p$;

$S_6$: determining the number n, the effective cross-section area A and the distribution of bolts;

$S_7$: determining a maximum allowable crack dimension according to the specification for nondestructive examination on bolts;

$S_8$: calculating the maximum allowable service stress $\sigma_{th}$ using the crack propagation threshold $K_{th}$ at design temperature by assuming that the growth direction of the crack determined in step $S_7$ is perpendicular to the loaded direction of the bolt. The $\sigma_{th}$ can be represented by $\sigma_{th}=K_{th}/(\sqrt{\pi a}F_I)$, where $F_I$ is obtained by referring to a handbook of stress intensity factors or by finite element calculation, and a is a length of the crack;

$S_9$: comparing the service stress $\sigma_s$ in step $S_5$ and the maximum allowable service stress $\Sigma_{th}$ in step $S_8$, if $\sigma_s$ is smaller than $\sigma_{th}$, then step $S_{10}$ is performed; otherwise, return to step $S_4$ and reduce the pretension stress $\sigma_p$; and $S_{10}$: after confirming that the crack does not propagate, and the bolts are safe during the design life, setting out the bolt material, the number n, the effective cross-section area A and the distribution of the bolts.

In a preferred embodiment, in step $S_3$, the mechanical properties of the materials are obtained by referring to a database of material properties; or if this way fails, tests should be carried out.

In another preferred embodiment, the linear expansion coefficients are obtained using a thermal dilatometer; the elastic modulus E is obtained using a dynamic thermomechanical analysis; the tensile property is obtained by tensile tests at the design temperature; the stress relaxation property is obtained by relaxation testing at the design temperature; crack propagation threshold $K_{th}$ at the design temperature is obtained as follows: crack growth tests are carried out using compact tensile specimens to obtain a curve of initial stress intensity factor vs. crack initiation time, and the curve is extrapolated or interpolated to obtain crack propagation threshold $K_{th}$ in the design life.

In another preferred embodiment, the crack propagation threshold $K_{th}$ in the design life is obtained from short-time crack growth tests at the design temperature. The curve of initial stress intensity factor vs. crack initiation time can be fitted using $K=Bt_i^\varphi$, where K is stress intensity factor, $t_i$ represents crack initiation time, B and $\varphi$ are material parameters obtained by fitting the test results. The stress intensity factor K calculated by putting the design life into the fitted equation is the crack propagation threshold $K_{th}$.

In another preferred embodiment, in step $S_6$, the number n, the effective cross-section area A and the distribution of the bolts are designed according to $P=nA\sigma_s$, using the service stress $\sigma_s$ obtained in step $S_5$ in view of the size of the sealing face and the force P.

In another preferred embodiment, in step $S_7$, the maximum allowable crack dimension is determined by balancing the minimum detectable size of defects by the nondestructive examination technique, the examination cost and the manufacture cost.

In another preferred embodiment, the nondestructive examination technique includes visual examination, magnetic powder examination and ray examination.

Beneficial Effects:

As the conventional design methods for bolts cannot ensure integrity of the nickel-based high-temperature bolts with high strength and low resistance to fracture, the inventors have developed a design method of high-temperature nickel-based bolts based on damage tolerance theory, and provide a new strength design process for bolts.

BRIEF DESCRIPTION OF THE DRAWINGS

The accompanying drawings are provided for better understanding of the invention. They constitute a part of the specification for further explanation of the invention without limiting the invention.

DETAILED DESCRIPTION OF THE INVENTION

Figure 1:
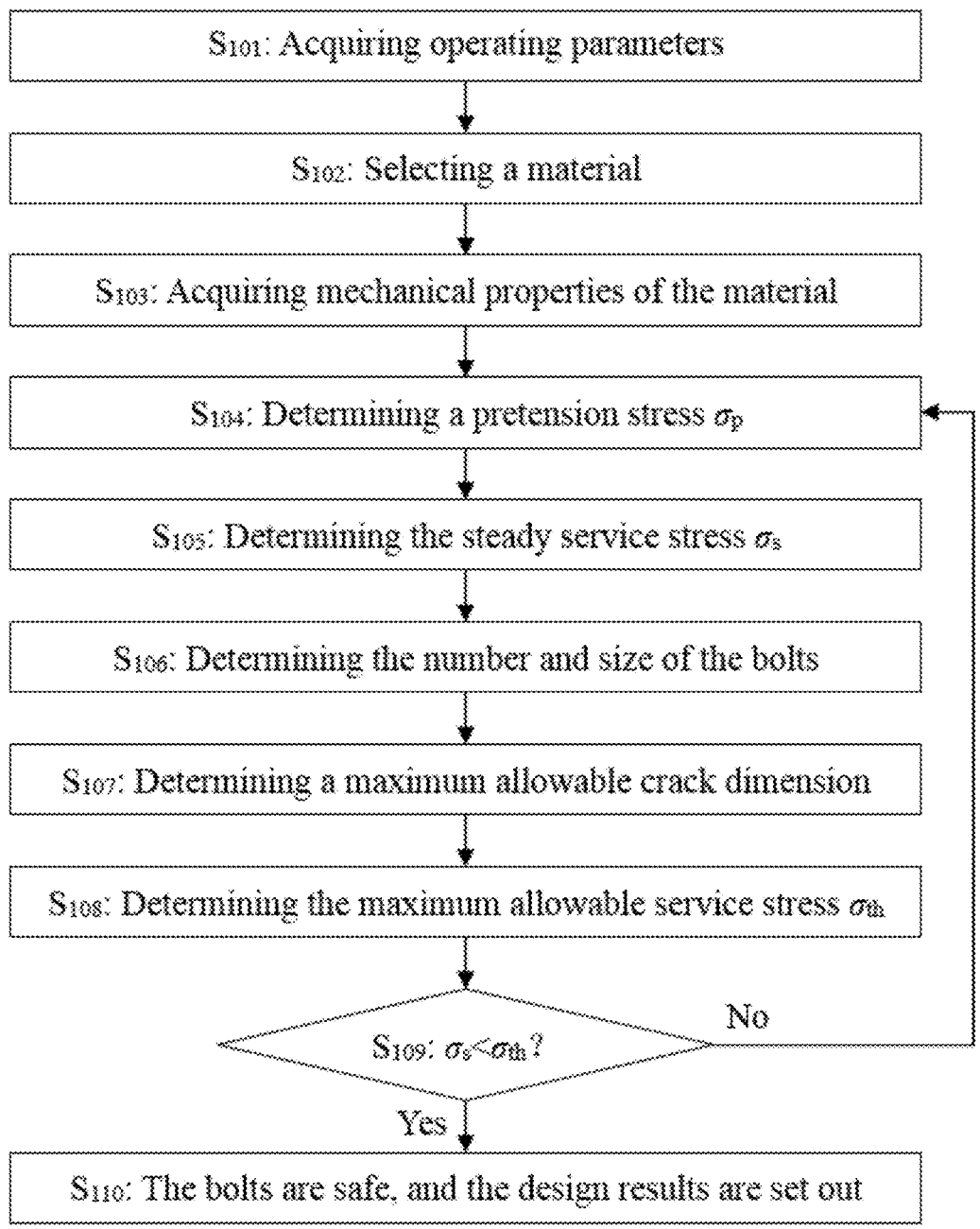
FIG. 1 is a flow chart of a preferred embodiment according to the invention.

The invention provides a design method of high-temperature nickel-based bolts based on damage tolerance theory, comprising the following steps:

$S_1$: acquiring operating parameters for the design, such as the design temperature T; the environmental medium; the prospective operating life; the designation, structure and size of the material to be fastened; and the force (sealing force) P needed to fulfill the fastening function;

$S_2$: selecting a material for bolts according to the design temperature and the environmental medium in step $S_1$;

$S_3$: acquiring mechanical properties of the materials, such as linear expansion coefficients $\alpha_b$ and $\alpha_v$ of the material for the bolt and the material to be fastened, respectively; elastic modulus E, tensile property, stress relaxation property, and crack propagation threshold $K_{th}$ of the material for the bolt at the design temperature;

$S_4$: determining a pretension $\sigma_p$ for a single bolt according to the selected material in step $S_2$, which can be given as $\sigma_p=0.5\sigma_y$, where $\sigma_y$ represents the yield strength of the bolt material;

$S_5$: determining the residual stress $\sigma_r$ after stress relaxation in the design life at the design temperature T in step $S_1$; calculating the thermal stress $\sigma_t$ under the steady state according to $\sigma_t=E(\alpha_v-\alpha_b)T$; and determining a service stress $\sigma_s$ under the steady state;

$S_6$: determining the number n, the effective cross-section area A and the distribution of bolts;

$S_7$: determining a maximum allowable crack dimension according to the specification for nondestructive examination on bolts;

$S_8$: calculating a maximum allowable service stress $\sigma_{th}$ according to the following formula using the high-temperature crack propagation threshold $K_{th}$ by assuming that the growth direction of the crack determined in step $S_7$ is perpendicular to the loaded direction of the bolt $$\sigma_{th}=K_{th}/(\sqrt{\pi a}F_I)$$

where $F_I$ is obtained by referring to a handbook of stress intensity factors or by finite element calculation, and a is the length of the crack;

$S_9$: comparing the service stress $\sigma_s$ in step $S_5$ and the maximum allowable service stress $\sigma_{th}$ in step $S_8$, if $\sigma_s$ is smaller than $\sigma_{th}$, then step $S_{10}$ is performed; otherwise, return to step $S_4$ and reduce the pretension stress $\sigma_p$;

$S_{10}$: after confirming that crack will not propagate, and bolts are safe during the design life, setting out the bolt material, the number n, the effective cross-section area A and the distribution of the bolts.

According to the invention, in step $S_3$, the mechanical properties of the materials are obtained by referring to a database of material properties; or if this way fails, tests should be carried out.

Preferably, the linear expansion coefficients may be obtained using a thermal dilatometer; the elastic modulus may be obtained using a dynamic thermomechanical analysis; the tensile property is obtained by tensile tests at the design temperature; the stress relaxation property is obtained by relaxation testing at the design temperature; crack propagation threshold $K_{th}$ at the design temperature is obtained as follows: crack growth tests are carried out using compact tensile specimens to obtain a curve of initial stress intensity factor vs. crack initiation time, and the curve is extrapolated or interpolated to obtain crack propagation threshold value in the design life.

Preferably, the curve of initial stress intensity factor vs. crack initiation time may be plotted using Origin software, Excel software or by hand; and can be fitted using $K=Bt_i^{\varphi}$, where K is stress intensity factor, $t_i$ is crack initiation time, B and $\varphi$ are material parameters obtained by fitting the test results. The stress intensity factor K calculated by putting the design life into the fitted equation is the crack propagation threshold $K_{th}$.

Preferably, in step $S_5$, $\sigma_r$ may be obtained by referring to a database of material properties; if this way fails, it may be obtained by extrapolating or interpolating a relaxation curve obtained by a high-temperature relaxation test and plotted using Origin software, Excel software or by hand. Wherein $\sigma_s$ is the smaller one between $\sigma_r$ and the larger one of $\sigma_p+\sigma_t$ and $\sigma_p$.

Preferably, the number n, the effective cross-section area A and the distribution of the bolts are designed according to $P=nA\sigma_s$ using the service stress $\sigma_s$ obtained in step $S_5$ in view of the size of the sealing face, the force P and other factors.

Preferably, in step $S_7$, the maximum allowable crack dimension may be determined by balancing the minimum detectable size of defects by a nondestructive examination technique such as visual examination, magnetic powder examination and ray examination, the examination cost and the manufacture cost.

Reference will be now made to the accompanying drawings.

FIG. 1 is a flow chart of a preferred embodiment according to the invention. As shown in FIG. 1, the design method of high-temperature nickel-based bolts based on damage tolerance theory according to the invention includes the following steps:

$S_{101}$: acquisition of operating parameters: acquiring operating parameters for the design according to the design conditions such as the design temperature; the environmental medium; the prospective operating life; the designation, structure and size of the material to be fastened; and the force (sealing force) P needed to fulfill the fastening function;

$S_{102}$: material selection: selecting a material for bolts according to the design temperature and the environmental medium in step $S_{101}$;

$S_{103}$: acquisition of the material properties: acquiring linear expansion coefficients $\alpha$ of the material for the bolt and the material to be fastened; elastic modulus E, tensile property such as yield strength $\sigma_y$, stress relaxation property, crack propagation threshold $K_{th}$ of the material for the bolt at the design temperature;

$S_{104}$: determination of a pretension stress $\sigma_p$: determining a pretension stress for a single bolt according to the selected material in step $S_{102}$, wherein $\sigma_p=0.5 \sigma_y$ in general;

$S_{105}$: determination of the steady service stress $\sigma_s$: determining the residual stress $\sigma_r$ after stress relaxation at the design temperature in the design life, wherein $\sigma_r$ may be obtained by referring to a database of material properties; if this way fails, it may be obtained by extrapolating or interpolating a relaxation curve obtained by high-temperature relaxation tests and plotted using Origin software, Excel software or by hand;

Calculating a temperature stress $\sigma_t$ under the steady state according to $\sigma_t=E(\alpha_v-\alpha_b)T$, wherein E is the elastic modulus, $\alpha_v$ is the linear expansion coefficient of the material to be fastened, $\alpha_b$ is the linear expansion coefficient of the material for the bolt, and T is the design temperature;

Determining the service stress $\sigma_s$ under the steady state, which is the smaller one between $\sigma_r$ and the larger one of $\sigma_p+\sigma_t$ and $\sigma_p$;

$S_{106}$: determination of the number and size of the bolts: determining the number n, the effective cross-section area A and the distribution of the bolts according to $P=nA\sigma_s$ using the service stress $\sigma_s$ under working states obtained in step $S_{105}$ in view of the size of the sealing face, the force P and other factors;

$S_{107}$: determination of a maximum allowable crack dimension: determining a maximum allowable crack dimension according to the specification for nondestructive examination on bolts;

$S_{108}$: determination of the maximum allowable service stress $\sigma_{th}$: calculating the maximum allowable service stress $\sigma_{th}$ using the high-temperature crack propagation threshold $K_{th}$ by assuming that the growth direction of the crack determined in step $S_{107}$ is perpendicular to the loaded direction of the bolt, wherein the maximum allowable service stress $\sigma_{th}$ can be calculated according to the following formula:

$$\sigma_{th}=K_{th}/(\sqrt{\pi a}F_I)$$

where $F_I$ can be obtained by referring to a handbook of stress intensity factors or by finite element calculation, and a is the length of the crack determined in step $S_{107}$;

$S_{109}$: comparing the service stress $\sigma_s$ in step $S_{105}$ and the maximum allowable service stress $\sigma_{th}$ in step $S_{108}$, wherein if $\sigma_s$ is smaller than $\sigma_{th}$, then step $S_{110}$ is performed; otherwise, the pretension stress $\sigma_p$ is reduced and steps $S_{105}$ to $S_{110}$ are performed until $\sigma_s<\sigma_{th}$; and $S_{110}$: report of the design results after confirmation of the safety of the bolts: cracks will not propagate, and the bolts are safe during the design life; the bolt material, the number n, the effective cross-section area A and the distribution of the bolts determined in steps $S_{102}$ and $S_{106}$ are the design results of this run.

Figure 4:
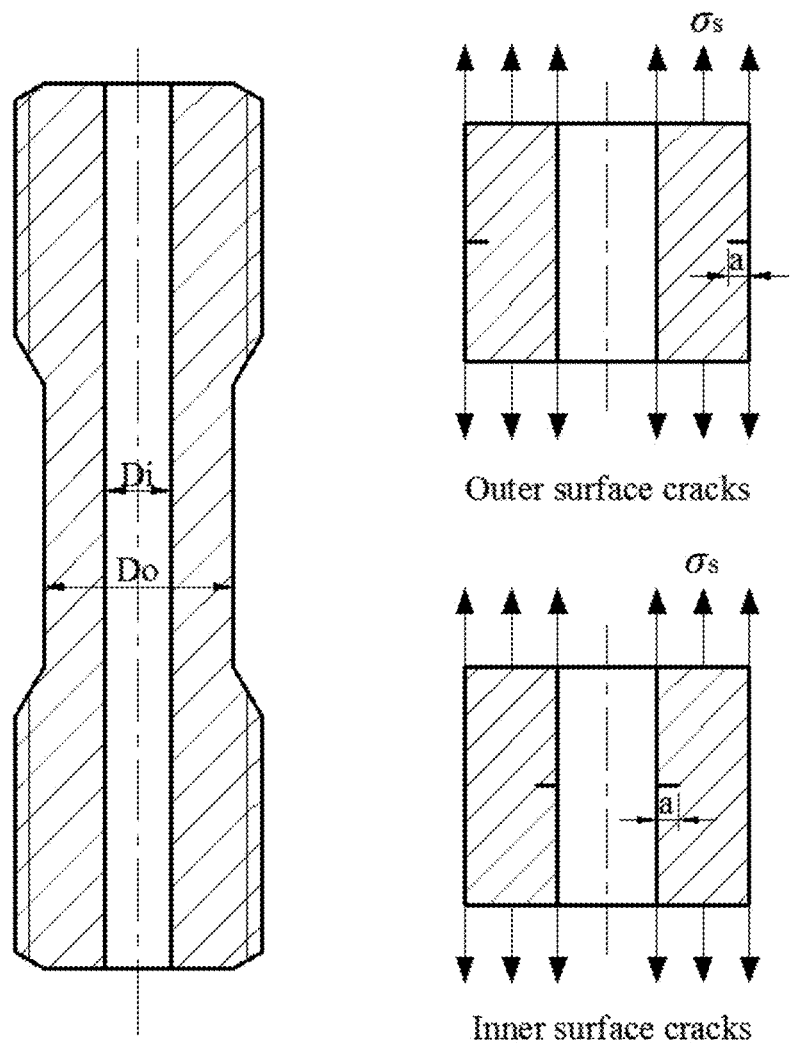
FIG. 4 shows schematically the profile of a bolt and the cracks in the inner and outer surfaces thereof in the Examples of the application.

FIG. 4 shows schematically the profile of a bolt and the cracks in the inner and outer surfaces thereof in the Examples of the application. As shown by FIG. 4, $D_o$ is the outer diameter of the bolt, $D_i$ is the inner diameter of the bolt, a is the crack length, and $\sigma_s$ is the service stress of the bolt. The cracks in the outer surface shows the existence of cracks in the outer surface of the bolt, and the cracks in the inner surface shows the existence of cracks in the inner surface of the bolt.

EXAMPLES

The invention will be further illustrated with reference to the following specific examples. It should be understood that these examples are only intended to exemplify the invention without limiting the scope of the invention. The test methods in the following examples for which no specific conditions are indicated will be carried out generally under conventional conditions or under those conditions suggested by the manufacturers. Unless otherwise specified, all percentages and copies are measured by weight.

Example 1

High-temperature steam valve of a steam turbine needed to design the valve bolts. The design temperature for the bolt was 560° C., environment was atmospheric air, the design life was 100000 hours; the sealing force needed by the valve was 8500000 N; the valve material was GX12CrMoWVNbN10-1-1; the outer diameter of the sealing face of the valve was 1695 mm, and the inner diameter was 1085 mm.

The process flow was as follows:

I. Operating parameters were acquired. The design temperature T for the bolts was 560° C.; the valve material was GX12CrMoWVNbN10-1-1; the outer diameter of the sealing face of the valve was 1695 mm, and the inner diameter was 1085 mm; and the sealing force P needed by the valve was 8500000 N.

Chemical composition of the GX12CrMoWVNbN10-1-1 steel (mass percentage, %)

| C | Si | Mn | P | S | Cr | Mo | Ni | W | V | N | Nb | Fe |
|---|----|----|----|----|----|----|----|----|----|----|----|----|
| 0.14 | 0.28 | 0.93 | 0.008 | 0.006 | 9.51 | 0.99 | 0.73 | 0.99 | 0.19 | 0.048 | 0.086 | Balance |

Chemical composition of the Inconel 783 alloy (mass percentage, %)

| C | Mn | S | P | Si | Cr | Ni | Fe | Al | Nb | Ti | B | Cu | Co |
|---|----|----|----|----|----|----|----|----|----|----|----|----|----|
| 0.01 | 0.025 | 0.002 | 0.004 | 0.038 | 2.99 | 28.24 | 26.04 | 5.24 | 2.99 | 0.20 | 0.0049 | 0.009 | Balance |

II. Inconel 783 alloy was selected as the material for the bolts based on the design temperature of 560° C.

Figure 2:
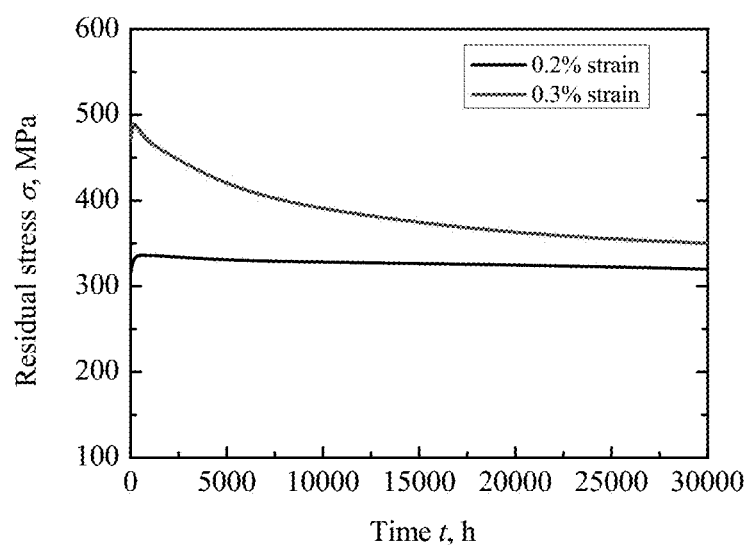
FIG. 2 plots stress relaxation curves at different initial loads obtained using relaxation specimens in a preferred embodiment according to the invention.
Figure 3:
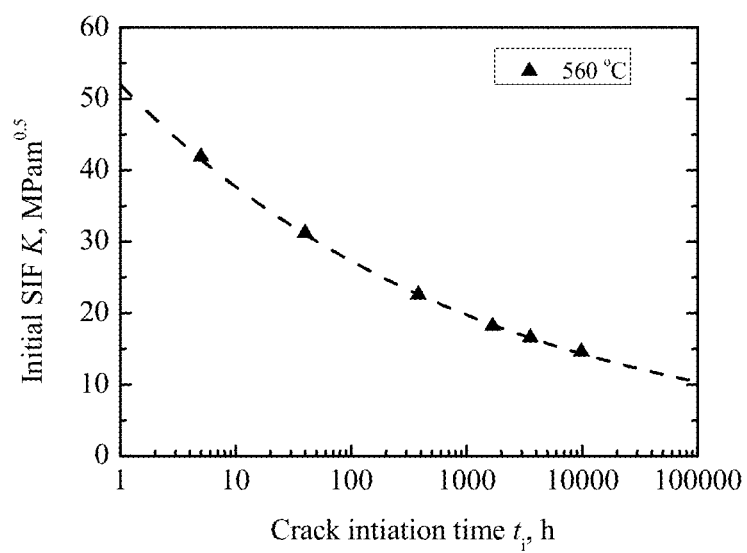
FIG. 3 plots a curve of initial stress intensity factor vs. crack initiation time obtained using compact tensile specimens in a preferred embodiment according to the invention.

III. The linear expansion coefficient $\alpha_b$ of the Inconel 783 alloy at 560° C. was 1.22 E-5 1/° C., and the linear expansion coefficient $\alpha_v$ of the GX12CrMoWVNbN10-1-1 steel at 560° C. was 1.24 E-5 1/° C. as determined using a thermal dilatometer (Netzsch, Germany). The elastic modulus E was 144 GPa at 560° C. as determined by static testing. Round bar tensile testing was conducted at 560° C., and the yield strength (0.2% offset) $\sigma_y$ was 630 MPa. Stress relaxation tests were conducted at 560° C. to obtain stress relaxation performances at various loads. Curves of residual stress $\sigma$ vs. time t were plotted using Origin software as shown in FIG. 2. Crack growth tests were carried out using compact tensile specimens at 560° C. in air condition. A curve of initial stress intensity factor K vs. crack initiation time $t_i$ was obtained. The curve was plotted using Origin software, and fitted to $K=52\ t_i^{-0.14}$. When the curve was extrapolated to 100000 hours, the crack propagation threshold value was 10.4 MPa√m (m represents meter), as shown in FIG. 3.

IV. The pretension stress of a single bolt was determined as $\sigma_p=0.5\ \sigma_y=0.5\times630$ MPa=315 MPa.

V. The stress relaxation curves of the Inconel 783 alloy at 560° C. and various loads were extrapolated to 100000 hours to obtain a residual stress $\sigma_r$ of 300 MPa. The thermal stress under the steady state was calculated as $\sigma_t=E(\alpha_v-\alpha_b)$ T=144000×(1.24 E-5-1.22 E-5)×560=16 MPa. The service stress under the steady state was determined as $\sigma_s=[(\sigma_p+\sigma_t, \sigma_p)_{max}, \sigma_r]_{min}=[(315+16, 315)_{max}, 300]_{min}=300$ MPa.

VI. Considering the size of the sealing face, the sealing force P and other factors, according to $P=nA\sigma_s$, the number of the bolts was determined to be 24, and the effective cross-section area of the bolts was 1180 mm². With the requirements of construction and the like taken into account, the outer diameter $D_o$ of the bolts was designed to be 46 mm, and the inner diameter $D_i$ was 25 mm, as shown in FIG. 4.

VII. According the specification of nondestructive examination, the maximum allowable crack size was 1 mm which was the depth of plane defect.

VIII. The most dangerous conditions would occur when the growth direction of the crack is perpendicular to the loaded direction of the bolt, as shown in FIG. 4. With reference to the high-temperature crack propagation threshold $K_{th}$=10.4 MPa√m, the maximum allowable service stress $\sigma_{th}$ was calculated as follows:

$$\sigma_{th}=K_{th}/(\sqrt{\pi a}F_I)$$

where $F_I$ was available from a handbook of stress intensity factors, and $F_I$ of the cracks in both the inner and outer surfaces was 1.19. The maximum allowable service stress $\sigma_{th}$ was 156 MPa.

IX. Obviously, the service stress $\sigma_s$ under the steady state was larger than the maximum allowable service stress $\sigma_{th}$. Thus, the pretension stress $\sigma_p$ was reduced to 140 MPa. The analysis from steps V to IX was performed, as detailed below:

9-5. The service stress under the steady state was determined as $\sigma_s=[(\sigma_p+\sigma_t, \sigma_p)_{max}, \sigma_r]_{min}=[(140+16, 140)_{max}, 300]_{min}=156$ MPa;

9-6. The number of the bolts was determined to be 24; the effective cross-section area of the bolts was 2280 mm²; the outer diameter $D_o$ of the bolts was 60 mm, and the inner diameter $D_i$ was 25 mm;

9-7. According to the specification of nondestructive examination, the maximum allowable crack size was 1 mm which was the depth of plane defect;

9-8. The most dangerous conditions would occur when the growth direction of the crack is perpendicular to the loaded direction of the bolt. With reference to the high-temperature crack propagation threshold $K_{th}$, the maximum allowable service stress $\sigma_{th}$ was calculated as follows:

$$\sigma_{th}=K_{th}/(\sqrt{\pi a}F_I)$$

where $F_I$ was available from a handbook of stress intensity factors, and $F_I$ of the cracks in both the inner and outer surfaces was 1.16. The maximum allowable service stress $\sigma_{th}$ was 160 MPa.

9-9. The service stress $\sigma_s$ under the steady state was smaller than the maximum allowable service stress $\sigma_{th}$.

X. The crack would not propagate at 560° C. in the 100000 hour, and the bolts would be safe. The high-temperature steam value needed 24 bolts with the outer diameter $D_o$=60 mm, the inner diameter $D_i$=25 mm, and the material was Inconel 783 alloy.

The Examples mentioned above are only preferred examples in the invention, and they are not intended to limit the scope of the invention. Equivalent variations and modifications according to the invention in the scope of the present application for invention all fall in the technical scope of the invention.

All of the documents mentioned in the invention are incorporated herein by reference, as if each of them were incorporated herein individually by reference. It is to be further understood that various changes or modifications to the invention can be made by those skilled in the field after reading the above teachings of the invention, and these equivalent variations fall in the scope defined by the accompanying claims of the application as well.

The invention claimed is:

1. A design method for generating and using a configuration of high-temperature nickel-based bolts for fastening a material included as part of an engineering design, said method comprising the following steps:
   S1: obtaining a first configuration of bolts, wherein the first configuration of bolts is obtained by—
      S1.1: acquiring operating parameters for the engineering design, the parameters including: a design temperature T; an environmental medium; a design life; a designation, structure and size of the material to be fastened; and a force P needed to fulfill a fastening function between the first configuration of bolts and the material to be fastened;
      S1.2: selecting a bolt material for the bolts of the first configuration according to the design temperature T and the environmental medium in step S1.1;
      S1.3: acquiring mechanical properties of the material of the bolts in the first configuration, including: linear expansion coefficients $\alpha_b$ and $\alpha_v$ of the bolt material and the material to be fastened, respectively; elastic modulus E, tensile property, stress relaxation property, and crack propagation threshold $K_{th}$ of the bolt material at the design temperature;
      S1.4: determining a first pretension stress $\sigma_{p1}$ for a single bolt from the first configuration of bolts according to the bolt material selected in step S1.2, wherein the first pretension stress $\sigma_{p1}$ is determined as $\sigma_{p1}$=0.5 $\sigma_y$, where $\sigma_y$ represents a yield strength of the bolt material;
      S1.5: determining a residual stress or after stress relaxation in the design life at the design temperature T in step S1.1, wherein $\sigma_r$ is obtained by referring to a database of material properties, or by extrapolating or interpolating a relaxation curve obtained by a high-temperature relaxation test and plotted; calculating a thermal stress $\sigma_t$ under steady state according to $\sigma_t$=E($\alpha_v$−$\alpha_b$)T; and determining a first service stress $\sigma_{s1}$ under steady state, wherein $\sigma_{s1}$ is the smaller one between $\sigma_r$ and the larger one of $\sigma_{p1}$+$\sigma_t$ and $\sigma_{p1}$;
      S1.6: determining a number and an effective cross-section area A of the bolts in the first configuration of bolts;
      S1.7: determining a maximum allowable crack dimension for any one of the bolts from the first configuration of bolts according to a specification for non-destructive examination on the bolts;
      S1.8: calculating a maximum allowable service stress $\sigma_{th}$ using the crack propagation threshold $K_{th}$ at the design temperature T by assuming that a growth direction of the crack determined in step S1.7 is perpendicular to a loaded direction of the bolt, wherein the $\sigma_{th}$ can be represented by $\sigma_{th}$=$K_{th}$/($\sqrt{\pi a}$ $F_I$), where $F_I$ is a dimensionless quantity obtained by referring to a handbook of stress intensity factors or by finite element calculation, and a is a length of the crack;
      S1.9: comparing the first service stress $\sigma_{s1}$ of step S1.5 and the maximum allowable service stress $\sigma_{th}$ of step S1.8;
   S2: determining whether the first configuration of bolts can be used in the engineering design to fasten the material to be fastened, wherein said determining step is based on the comparison of service stresses in step S1.9;
   S3: generating a second configuration of bolts for the engineering design, wherein the second configuration of bolts is generated by—
      S3.1: selecting a second pretension stress $\sigma_{p2}$ for a single bolt from the second configuration of bolts according to the bolt material selected in step S1.2, wherein the second pretension stress $\sigma_{p2}$ is less than the first pretension stress $\sigma_{p1}$;
      S3.2: determining a second service stress $\sigma_{s2}$ under steady state, wherein $\sigma_{s2}$ is the smaller one between $\sigma_r$ and the larger one of $\sigma_{p2}$+$\sigma_t$ and $\sigma_{p2}$;
      S3.3: determining a number and an effective cross-section area A of the bolts in the second configuration of bolts;
      S3.4: comparing the second service stress $\sigma_{s2}$ and the maximum allowable service stress $\sigma_{th}$ determined in step S1.8, wherein if $\sigma_{s2}$ is less than $\sigma_{th}$, then the second configuration of bolts is available for use in the engineering design;
   S4: selecting the second configuration of bolts for use in the engineering design to fasten the material to be fastened, wherein the second configuration of bolts has a higher fracture resistance than the first configuration of bolts; and
   S5: fastening the material to be fastened using the bolts from the second configuration of bolts selected in step S4.

2. The method of claim 1, wherein the linear expansion coefficients are obtained using a thermal dilatometer; the elastic modulus E is obtained using a dynamic thermomechanical analysis; the tensile property is obtained by tensile tests at the design temperature; the stress relaxation property is obtained by relaxation testing at the design temperature; crack propagation threshold $K_{th}$ at the design temperature is obtained as follows: crack growth tests are carried out using compact tensile specimens to obtain a curve of initial stress intensity factor vs. crack initiation time, and the curve is extrapolated or interpolated to obtain the crack propagation threshold $K_{th}$ in the design life.

3. The method of claim 2, wherein crack propagation threshold $K_{th}$ in the design life is obtained from short-time crack growth tests at the design temperature, wherein the curve of initial stress intensity factor vs. crack initiation time can be fitted using $K=Bt_i^\varphi$, where K is stress intensity factor, $t_i$ represents crack initiation time, B and $\varphi$ are material parameters obtained by fitting the test results, and wherein the stress intensity factor K calculated by putting the design life into the fitted equation is the crack propagation threshold $K_{th}$.

4. The method of claim 1, wherein in step S1.7, the maximum allowable crack dimension is determined by taking into consideration the following factors: the minimum detectable size of defects by the nondestructive examination technique, the examination cost and the manufacture cost.

5. The method of claim 4, wherein the nondestructive examination technique includes visual examination, magnetic powder examination and ray examination.

6. The method of claim 1, wherein the material to be fastened comprises a steam valve for a steam turbine.

7. The method of claim 6, wherein the bolts comprise valve bolts.

8. The method of claim 1, wherein in step S1.3, the mechanical properties of the materials are obtained by referring to a database of material properties; or by material testing.

9. The method of claim 1, wherein in step S1.6, the number and the effective cross-section area A of the bolts in the first configuration of bolts are designed according to $P=nA\sigma_s$ using the first service stress $\sigma_{s1}$ obtained in step S1.5 in view of the size of the sealing face and the force P.

\* \* \* \* \*